United States Patent [19]
Guerard et al.

[11] Patent Number: 5,752,916
[45] Date of Patent: May 19, 1998

[54] METHOD OF OBTAINING, IN NUCLEAR MEDICINE, A TRUNCATION-CORRECTED IMAGE OF A PATIENT'S BODY

[75] Inventors: Bruno Guerard, Chaville; Stéphane Papillon, Paris, both of France

[73] Assignee: SMV International, Buc Cedex, France

[21] Appl. No.: 673,792

[22] Filed: Jun. 27, 1996

[30] Foreign Application Priority Data

Jun. 29, 1995 [FR] France .................... 95 07834

[51] Int. Cl.⁶ .................................................. A61B 5/00
[52] U.S. Cl. ................ 600/407; 250/363.04; 382/131
[58] Field of Search ................ 250/363.01, 363.02, 250/363.05, 363.07, 370.08, 370.09, 369; 378/4, 11, 13, 15, 21, 901, 8; 600/407; 128/922; 382/131

[56] References Cited

U.S. PATENT DOCUMENTS

| | | | |
|---|---|---|---|
| 3,970,853 | 7/1976 | Kuhl et al. | 250/363 |
| 4,618,772 | 10/1986 | Haas et al. | 250/363 S |
| 4,782,233 | 11/1988 | Genna et al. | 250/363 S |
| 5,421,330 | 6/1995 | Thirion et al. | 128/653.1 |
| 5,457,724 | 10/1995 | Toth | 378/4 |
| 5,565,684 | 10/1996 | Gullberg et al. | 250/363.04 |
| 5,594,251 | 1/1997 | Fleury et al. | 250/363.05 |
| 5,672,877 | 9/1997 | Liebig et al. | 250/363.04 |

FOREIGN PATENT DOCUMENTS 0 200 939   11/1986   European Pat. Off.
2 083 970    3/1982   United Kingdom.

OTHER PUBLICATIONS

Kadrmas et al., Nuclear Science Symposium & Medical Imaging Conference, Oct. 1994; IEEE Conference Record, vol. 3, pp. 1247–1250.

*Primary Examiner*—Marvin M. Lateef
*Assistant Examiner*—Eleni Mantis Mercader
*Attorney, Agent, or Firm*—Nilles & Nilles SC

[57] ABSTRACT

A method in nuclear medicine of obtaining a truncation-corrected image of a patient's body, according to which the patient's body is placed on a bed of a nuclear medicine machine including at least one detector head equipped with a detection surface of nuclear rays; a first truncated image in projection of the patient's body is acquired; a second image in projection of the patient's body at an angular position of the first truncated image in projection is acquired. An item of information from the second image is introduced in the first image (P1) with a view to correcting it in its truncated part. The invention applies, in particular, to tomographic examinations.

21 Claims, 4 Drawing Sheets

METHOD OF OBTAINING, IN NUCLEAR MEDICINE, A TRUNCATION-CORRECTED IMAGE OF A PATIENT'S BODY

BACKGROUND OF THE INVENTION

This invention concerns a method of obtaining, in nuclear medicine, a truncation-corrected image of a patient's body.

FIELD OF THE INVENTION

Nuclear medicine is a discipline in which an attempt is made to obtain information from a patient in whose body a radioactive solution has been injected. The principle of the method is as follows. A gamma radio-emission marker is injected into a patient. This marker, conveyed by a biological agent, spreads in the patient's body and is preferentially fixed in one or several target organs. A gamma ray camera fitted without a detector head captures the gamma ray emitted by the patient's body for a given angle of vision. This ray crosses a collimator of the detector head, excites a scintillation crystal which converts the energy of the gamma photons into a luminous energy detected by photomultiplier tubes which then produce, depending on the luminous intensity received, electrical signals. By performing barycentric localizations on all these electrical signals, it is possible, in a known way, to determine the origin of the scintillation in a field of detection. An incremental acquisition is then performed by cumulating the number of scintillations detected on the whole field of detection of the detector head, and in this way an image in projection or revealing projection is acquired of the concentration of the radioactive product in the patient's body.

It has become usual practice to acquire a projection of the patient's body by angle of vision for multiple angles of vision regularly spaced on a given angular sector. Taken together, these projections make it possible to reconstruct, by means of a complex calculating algorithm, an image of a section or a volume of the patient's body.

The above-mentioned projections emitted by the patient's body present artifacts due to the attenuation of the gamma rays crossing the body. These artifacts are corrected by obtaining an image in projection of the patient's body, acquired in transmission, from a gamma radio-emission linear source which is placed facing the detector head so that the patient is interposed between the source and the detector head. Such a projection in transmission represents the patient's transparency to the gamma rays in a given angle of vision.

The angle of vision of a gamma ray camera depends on the dimensions of the useful detection surface of the detectors. The more extensive this surface, the wider the field of vision of the gamma ray camera. However, a wide detection surface adds to the price of a gamma ray camera, and gamma ray cameras are often produced whose field of vision is insufficient to allow the acquisition of projections encompassing all of the patient's body. This is particularly the case with corpulent patients.

As a result, the projections, whether acquired in emission or transmission, are truncated. These truncations are expressed by the presence of artifacts on the reconstructed patient's body whose contours show a ring of superbrilliance rendering the whole of said image unusable from the point of view of an attenuation correction.

DESCRIPTION OF THE PRIOR ART

There is a known method of correcting artifacts generated by truncations. This method proposes, firstly, a modeling of the contours of the patient's body and, secondly, an extrapolation of the projections acquired by a decreasing polynomial function as far as the modeled contours of the patient's body. An attenuation value equal to zero is attributed to the contours.

However, this method may lead to a corrected reconstructed image being obtained which is of poorer quality then the uncorrected image. This is particularly the case in the acquisition of an attenuation correction image in cardiac tomography. Indeed, in such a case, when a lung is truncated, it is impossible to reconstitute the thoracic cage correctly, extrapolation taking place in the pulmonary cavity which should be attributed an attenuation value equal to zero.

SUMMARY OF THE INVENTION

The purpose of this invention is to propose a new method of obtaining, in nuclear medicine, an image of the patient's body, a method which overcomes, at lower cost, the disadvantages mentioned above and in which truncations are corrected without extrapolation.

This objective, along with others which will become apparent in due course, is attained by means of an acquisition method according to which a first truncated projection is corrected by a second projection acquired in a position $\alpha(i)$ truncating part of the patient's body thanks to a combination of the projections acquired in tomographic positions $\alpha(i+1)$ and/or $\alpha(i-1)$ and not truncating the part of the patient's body which is absent from projection $\alpha(i)$.

The invention thus concerns a method of obtaining, in nuclear medicine, an image of the patient's body, in which:

- the patient's body is placed on a bed of a nuclear medicine machine comprising at least one detector head equipped with a detection surface of nuclear rays;
- a first image in truncated projection is acquired of the patient's body, with a detector head;
- a second image in projection is acquired, with said detector head, of the patient's body at an angular position close to the first image in truncated projection; and, characterized in that
- information from second image is introduced into first image with a view to correcting it in its truncated part.

BRIEF DESCRIPTION OF THE DRAWINGS

The ensuing description, which has no limiting character, will provide a clearer understanding of the way in which the invention may be put into practice It is to be read in relation to the accompanying drawings, in which.

DESCRIPTION OF THE PREFERRED EMBODIMENTS

Figure 1:
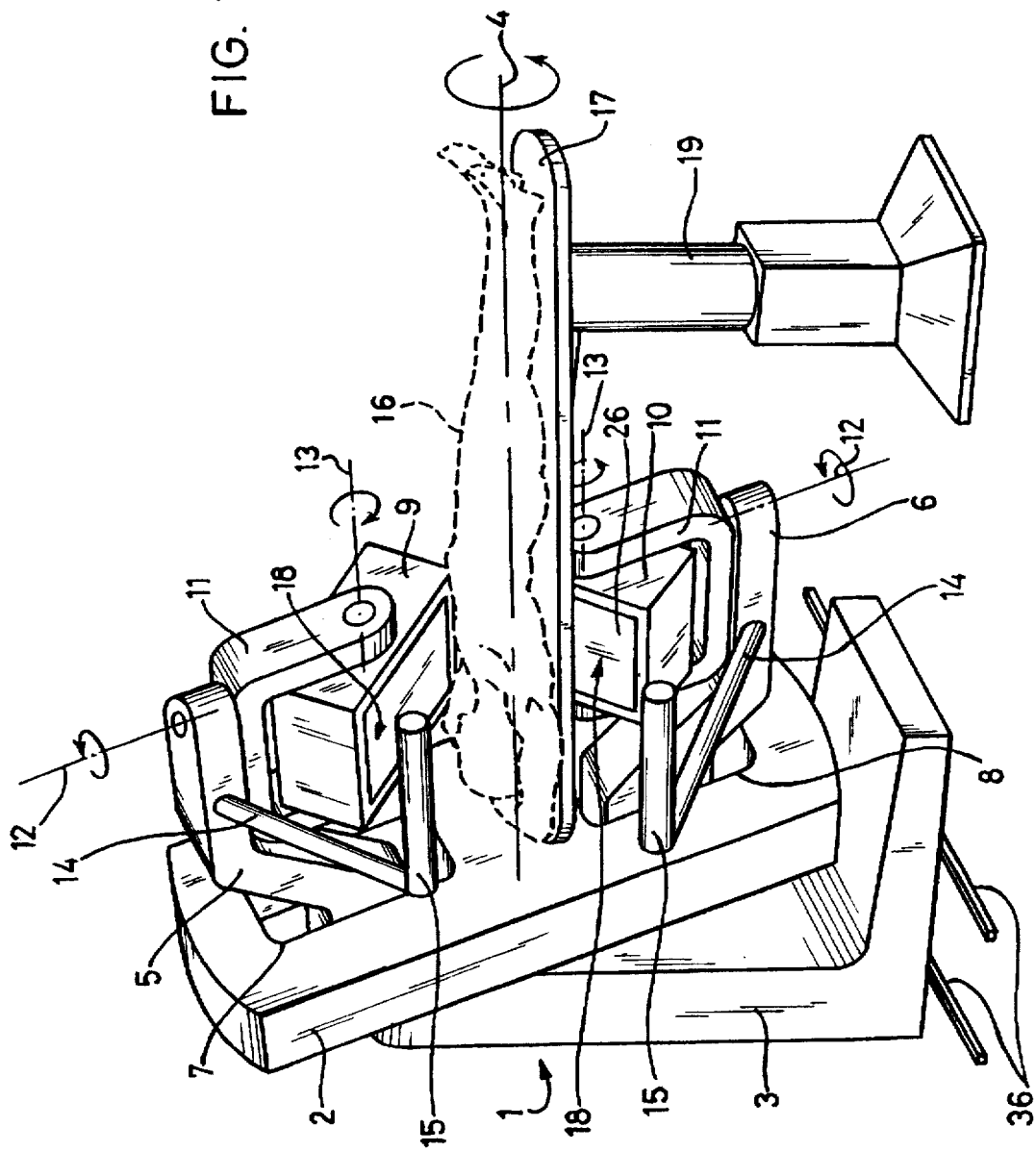
FIG. 1 shows, in perspective, a gamma ray camera for implementing a method according to the invention.

A gamma camera 1 for the implementation of a method according to the invention comprises, as represented in FIG. 1, a mobile base 2 on a mount 3 in such a way as to rotate around an axis 4 of rotation of the gamma ray camera 1, the axis 4 being approximately parallel to the ground and passing approximately by the center of gravity of said base 2.

The mount 3 is mobile in lateral translation along rails 36 orthogonal to the axis 4.

The base 2 carries, in the embodiment example of this description, two arms 5 and 6 placed symmetrically on either side of the axis 4. However, in other embodiment examples, the base 2 will carry a single arm or, even, more than two arms.

The arms 5, 6 may radially approach or draw apart from the axis 4, within the limits of windows 7 and 8, thanks to an apparatus commonly referred to as a lift.

Each arm 5, 6 is fitted, at its free extremity, with a detector head 9, 10, approximately parallelepipidal and rectangular. The detector head 9, 10 is attached to the arm 5, 6 by means of a U-shaped stirrup 11. The stirrup 11 is mobile in rotation in relation to the free extremity of the arm 5 which carries it along a rotational axis 12 orthogonal to the axis 4 and called angulation axis of the detector head 9, 10. In addition, the detector head 9, 10 is mobile in rotation between the descending sides of the stirrup 11 along an axis 13 which parallel to the axis 4 and which forms an orientation axis of the detector head 9, 10.

Moreover, each arm 5, 6 includes a support 14 of a box 15 comprising a gamma radio-emission linear source for obtaining projections in transmission.

A patient's body 16 is placed stretched out on a bed 17, between active faces 18 of the detector heads 9 and 10, approximately along rotation axis 4 of the gamma ray camera 1. The bed 17 is supported by an elevator stand 19 which makes it possible to set the height of the patient's body 16 to the required position. Such a bed 17 is described more specifically in the French patent application published under number 2 684 865, the contents of which are incorporated here for reference purposes.

The gamma ray camera 1, such as previously described, allows numerous positions relative to the detector heads 9, 10 in relation to the patient's body 16. This advantage is a particular feature of so-called open-mount gamma ray cameras, in which the detector heads 9, 10 are not enclosed in a tunnel.

Figure 2:
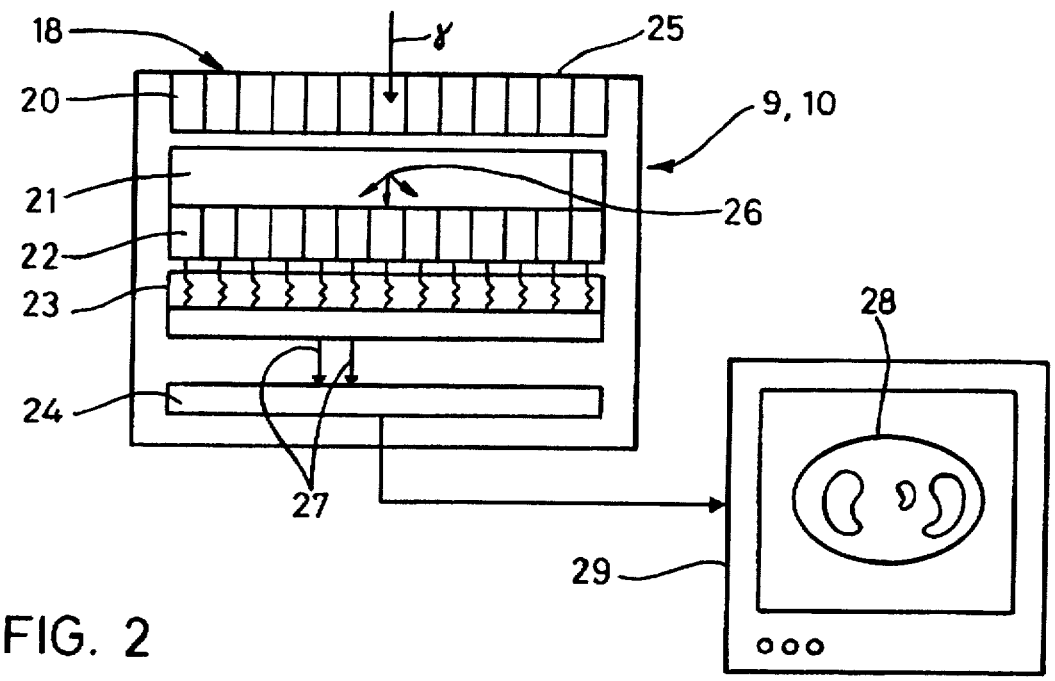
FIG. 2 illustrates, in section and schematically, a detector head of a gamma ray camera for implementing a method according to the invention.

As may be seen in FIG. 2, a detector head 9, 10 comprises essentially, starting from its active face 18, a collimator 20, a scintillation crystal 21, a network of photomultiplier tubes 22 and treatment circuits 23 connected to an amplification circuit 24.

The collimator 20 is generally formed with straight holes. It defines a detection surface 25 of the detector head 9, 10, that is to say a portion of the active face 18 of the detector head 9, 10 likely to be able to detect a gamma ray γ.

The principle for obtaining an image of the patients body 16 is as follows. For a given position in orientation and angulation of a detector head 9, 10, the gamma rays coming from and/or crossing the patient's body 16, which have a propagation direction approximately orthogonal to the detection surface 25, cross the collimator 20 and provoke a scintillation 26 in the crystal scintillator 21. This scintillation 26 is detected and then amplified by the network of photomultiplier tubes 22 which elaborates the electrical signals of localization 27. These localization signals 27 are next treated, and an image in projection or projection of the patient's body 16 for the previously mentioned position is then obtained, with several projections, obtained for different relative positions of the detector heads 9, 10 and of the patient's body 16, an image 28 of the patient's body 16 may be reconstructed, for example, a sectional image of said body 16 which, presented on a monitor 29 linked to the gamma ray camera 1, allows a medical analysis.

Figure 3:
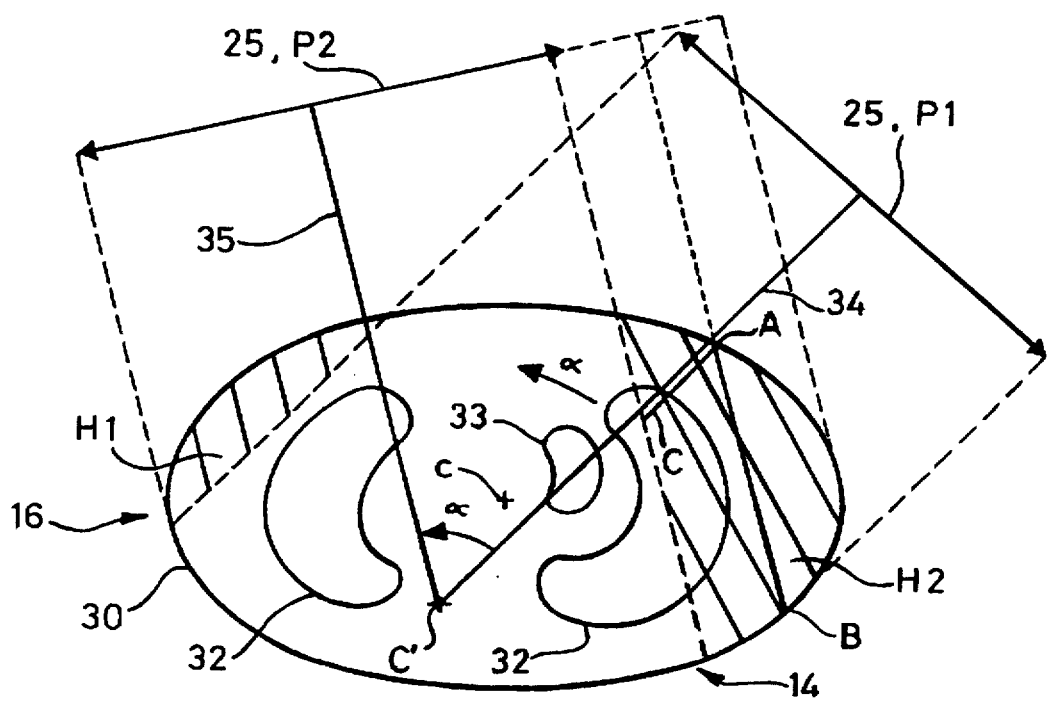
FIG. 3 schematically shows the principle of a method according to the invention.

FIG. 3 illustrates the principle of the method of the invention.

In this figure, the contours of the patient's body 16 are represented, in cross section, by an ellipse 30 of center C. However, this example is not limiting, and the contours of the patient's body 16 can be modeled and represented by any form. The patient's lungs and heart are marked respectively 32 and 33.

The purpose of the examination is to collect information coming from the interior of the ellipse 30.

For the acquisition of a projection in emission or transmission, a detector head 9, 10 whose detection surface 25 is symbolized by a double arrow, is placed close to the patient's body 16. According to the invention, at least two projections of the patient's body 16 are obtained. A first projection P1 is acquired in a first position P1 of the detection surface 25 of the detector head 9 or 10 in relation to the patient's body 16, then a second projection P2 is acquired in a second position P2 of the surface 25 of the same detector head 9 or 10 in relation to the body 16. The two positions P1, P2 are angularly next to each other, that is to say that the angle α made by the normal 34 to the detection surface 25 in the first position P1 and the normal 35 to said surface 25 in the position P2, is small, less than about 10°, and in practice of the order of 3°. The normals 34, 35 to the detection surfaces 25 intersect in a center C' which is not necessarily the center C of the ellipse 30.

It will be noted that the angle α may be equal to 0. In this case, normals 34, 35 are parallel and there is no center C'.

The first projection P1 is truncated. The detection surface 25, in practice of the order of 350×250 cm, is not in fact sufficient to allow detection of all of the patient's body 16. As a result, a hatched part H1, which is not included in the field of detection of the head 9, 10, is not detected. In contrast, the second projection P2 of the patient's body 16 is acquired in conditions such that a portion of the part H1 is detected. An item of information is thus acquired in the second projection P2 but not in the first projection P1.

According to the invention, this item of information is introduced or interpolated in the first projection P1 with a view to correcting the projection P1 in its truncated part. Reciprocally, in the event of the second projection P2 being truncated in its part H2, an item of information from the first projection is introduced in the second projection P2 with a view to correcting this second projection P2 in its truncated part. In other words, the missing information in the truncated part of a projection is added from another projection acquired along a similar angle.

It will be noted that the introduction of an item of information from one projection in another, angularly displaced projection is not in itself a straightforward operation. Indeed, if the detection surface 25 of the detector head 9, 10 had been wide enough to capture the whole of the patient's body 16, it would have allowed the acquisition, in the projection P2, of a segment AB of the part H2. However, in the invention, this segment AB has not been acquired and it is replaced, in said projection P2, by a segment AC acquired during the projection P1. P1 and P2 do not have the same dimensions or the same orientations in the patient's body 16. However, and notably for angular projections close to the detection surfaces 25, these segments AB, AC merge or at least tend towards an identical segment, thereby allowing the correction of the truncations.

Moreover, in order to capture the patient's body 16 in its entirety, the detector heads 9, 10 are moved from one edge to the other of the patient's body 16, proceeding in such a way that the first projection P1 comprises the image of one edge of the patient's body 16 and that the second projection P2 comprises the image of the opposite edge of said body 16. The totality of the patient's body 16 is then acquired in the two angularly close projections P1 and P2 and, the information from one projection being introduced in the other and vice versa, each projection P1 or P2 of the patient's body 16 is acquired virtually in totality.

This explains why it may be stated that the patient's body 16 is seen in a virtual angular zone of 180°. In this sense, the detector heads 9, 10 possess a wide virtual field of vision.

In addition, the method of the invention is advantageously improved by imposing a continuity between the information introduced in a truncated part of a projection and that acquired in said projection.

A description of the invention will now be given in relation to the example of a cardiac tomography examination with attenuation correction. In such an examination, the detector heads 9, 10 are advantageously placed in a position said to be at 90°, in which the detection surfaces 25 of said heads 9, 10 are placed at right angles to each other. In this case, for each detector surface 25, an inner edge 37 is defined, that is to say the edge which is closest to the detection surface 25 of the adjoining head, and an outer edge 38 opposite the inner edge 37. Such a position is shown in FIG. 1. The detector heads 9, 10 are then moved in rotation around the patient's body 16, led step by step to regular angles of view by the base 2 turning around its axis 4. In this way, at each angle of vision $\alpha(i)$, a projection in emission by detector head 9, 10 is acquired and, when a gamma ray radio-emission source has been placed in the box 15 situated facing the detector heads 9, 10, a projection in transmission by the head is acquired. By taking the projections together, an image of the patient's body 16 that is corrected in attenuation may then be obtained.

Figure 4:
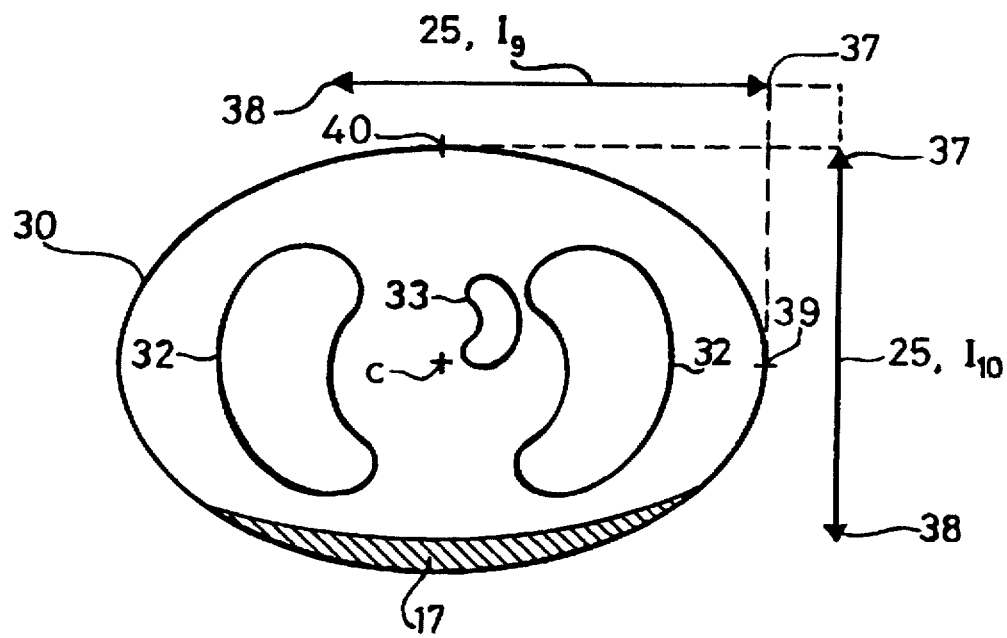
FIG. 4 represents the ideal positioning of the detector heads for the application of a method according to the invention.

In a phase taking place prior to this examination and illustrated in FIG. 4, an initial positioning of the detector heads 9, 10 in relation to the patient's body 16 is carried out. For this purpose, the heads 9, 10 a are placed respectively in positions $I_9$ and $I_{10}$ which, supposing that the patient's body 16 is centered on the bed 17, allow the complete determination of the dimensions of the patient's body 16 and bed board 17 system as well as the center C of said patient.

In a particularly advantageous example, the detector head 9 is placed in a horizontal position $I_9$ and above the patient's body 16 in such a way that the inner edge 37 of the detection surface 25 is vertical to an apse 39 on the side of the heart 33 of the contour 30 of the patient's body 16, and the detector head 10 is placed in a vertical position $I_{10}$ (at 90° to the head 9) and on the side of the heart 33 of the patient, in such a way that the inner side 37 of its detection surface 25 is horizontal to an upper apse 40 of the contour 30 of the patient's body 16. Thus, the contours of the patient's body 16 placed on the bed 17 will be totally defined, that is to say modeled.

Furthermore, it is possible to ordain that the heart 33 must never be truncated. This constraint may lead to a slight truncation of the edge of the patient's body 16 opposite the heart 33, but this will have no major consequence on the reconstructed image obtained.

In fact, the inner trajectory is based on the knowledge of the vertical and horizontal dimensions of the patient/bed system whose form is modeled by an ellipse. The dimensions of the ellipse are obtained by manually positioning the camera on the inner trajectory for a particular angle so that one detector is horizontal and above the patient and the other detector is vertical on the patient's side. In this particular position, the sighting center may be arbitrarily defined as being, for example, the center of the ellipse or again as a particular organ whose localization is defined manually. In this case, for each angle of vision the trajectory is determined by the position of the camera which ensures that the two orthogonal straight lines passing alternately by the inner and then the outer edges of the detection fields, are tangential to the ellipse. Finally, for each angle of vision, the geometric projection of the sighting center on each detector is translated along the x-axes so as to coincide with the center of the image. Incidentally, in the event that the position of the organ to be observed is known, a check is carried out in order to ensure that the organ itself is not submitted to truncation, this constraint taking priority over the constraint of non truncation of the patient.

Figure 5:
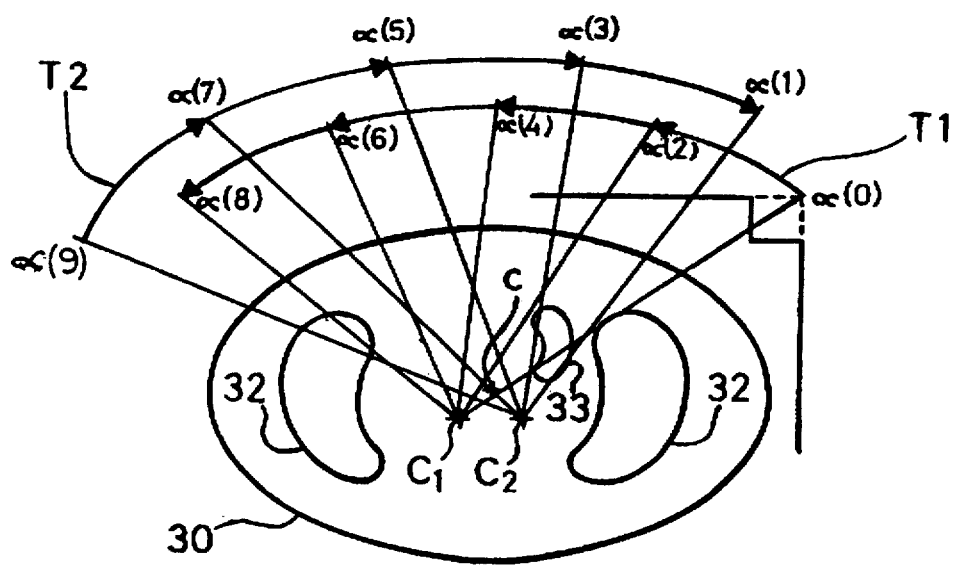
FIG. 5 represents the trajectories followed by the detector heads during a tomographic examination in conformity with a method according to the invention.

In fact, once the preparatory phase has been completed, it is possible to calculate the positions $\alpha(i)$ for i varying from 0 to n which the detector heads 9, 10 will occupy in the course of the tomographic examination. The number n of these positions and the acquisition time is the same as in the case of a tomographic examination carried out without truncation correction. In fact, p of the n positions are inscribed along a first trajectory T1 of the detector heads 9, 10 and n-p other positions are inscribed along a second trajectory T2. These trajectories T1 and T2, represented in FIG. 5, are advantageously carried out in succession. One of these trajectories, for example the first trajectory T1, begins at $\alpha(0)$ and ends at $\alpha(8)$. 5×4=20 projections will be acquired during this trajectory at positions $\alpha(0)$, $\alpha(2)$, $\alpha(4)$, $\alpha(6)$ and $\alpha(8)$, 5 projections in emission and 5 projections in transmission for the detector head 9 and similarly for the detector head 10. With the other trajectory T2, 20 projections are acquired at positions $\alpha(9)$, $\alpha(7)$, $\alpha(5)$, $\alpha(3)$ and $\alpha(1)$. According to the invention, the trajectory T1 is termed "inner" trajectory since it is such that the "inner" edge of the field of detection of the detector head follows the contours of the patient's body 16. On the other hand, the trajectory T2 is termed "outer" trajectory since it is such that the edge of the field of detection opposite the inner edge follows the contours of the patient's body 16. Contrary to the inner trajectory, the outer trajectory cannot in theory be placed under an analytical form.

So that the trajectories T1 and T2 may be followed strictly, it will be noted that, according to the invention, the position of the patient's body 16 is modified, in vertical translation, by a rise or fall of the bed 17 carried out by its elevator stand 19, and in horizontal translation by the movement of the mount 3 along the rails 36.

With a view to simplifying FIG. 5, the projections acquired during the trajectory T1 are represented centered on a center C1, whereas those acquired during the trajectory T2 are represented centered on a center C2. In general, however, there is no single center C1 or C2 for a trajectory T1 or T2.

The projections acquired in positions $\alpha(0)$, $\alpha(2)$, $\alpha(4)$, $\alpha(6)$ and $\alpha(8)$ are angularly adjacent to the projections acquired in positions $\alpha(1)$, $\alpha(3)$, $\alpha(5)$, $\alpha(7)$ and $\alpha(9)$ respectively.

If one of the projections in emission or transmission acquired in position α(i) is truncated, an item of information from the corresponding projection in emission or transmission acquired in position α(i−1) or α(i+1) is then introduced in said projection acquired in α(i) in order to correct it in its truncated part. Information acquired in positions α(i−1) and α(i+1) may, of course, be introduced in the projection acquired in α(i).

The reconstructed tomographic image 28 obtained will now present no artifacts due to truncations.

Figure 6A:
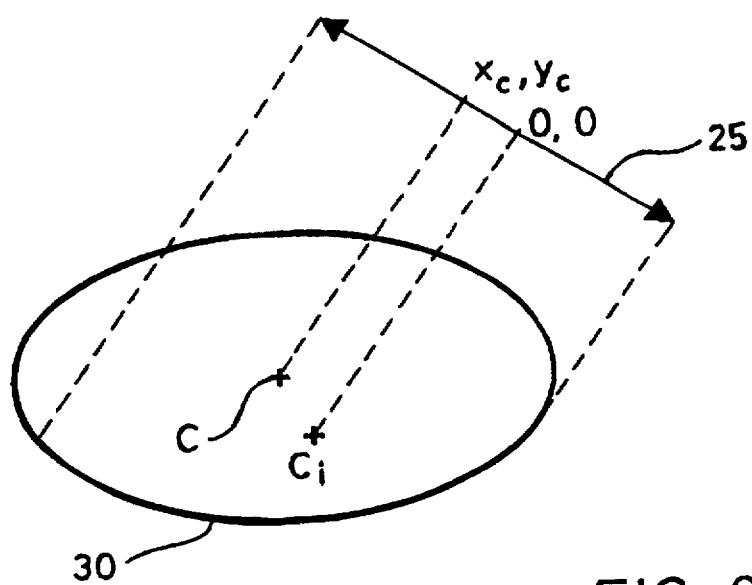
FIG. 6A schematizes the projection of a center C during an acquisition according to the invention.
Figure 6B:
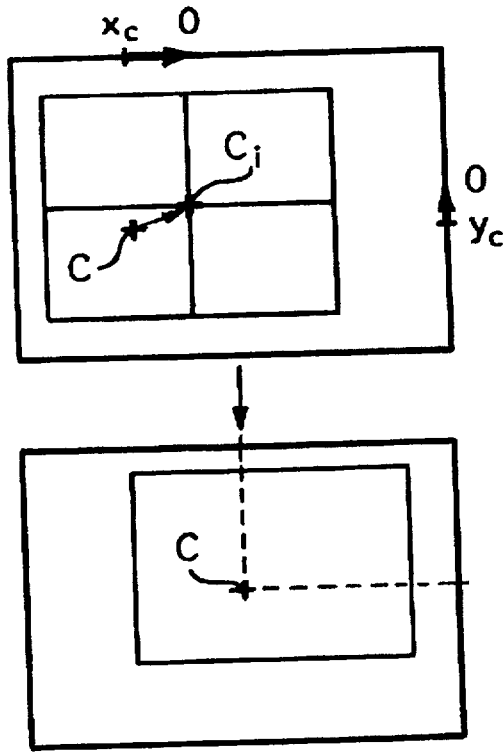
FIG. 6B schematizes a centering of the images in projection acquired in a method according to the invention.

In the course of the explanation of the principle of the invention of FIG. 3, it was seen that the center of intersection of the normals 34, 35 to the detection surfaces 25 was not necessarily the center C of the ellipse 30 of the patient's body 16 which merge, by hypothesis, with the center of the reconstructed image 28. Now, the center C chosen must project to the center of each projection image for each projection angle. This is performed naturally during a circular trajectory of the detector head(s) 9, 10 around the patient's body 16, but is no longer true in the case of the complex trajectories T1 and T2 for which the projection of the center C shifts differently from one angle to the next. Thus, for each acquisition represented in FIG. 6A corresponding to a given angle of vision, the projection images are shifted so that the projection of the center C of the patient's body identified by its coordinates $x_c$ and $y_c$ coincides with the center Ci of the projection of coordinates 0 and 0. This may be carried out by means of a method of correction explained in FIG. 6B. In this figure, the projection of the center C, which appears at the x-axis $x_c$ and the y-axis $y_c$, is shifted by a quantity $-x_c$ and $-y_c$.

We claim:

1. Method of obtaining, in nuclear medicine, an image of a patient's body, said method comprising:

placing the patient's body on a bed of a nuclear medicine machine, said machine including at least one detector head equipped with a detection surface of nuclear rays;

acquiring a first, truncated image in projection of the patient's body, said first image having a truncated part and being acquired at a first angular position with respect to the patient's body;

acquiring a second image in projection of the patient's body, said second image being acquired at a second angular position, close to first angular position of the first image; and, wherein an item of information from said second image is introduced in said first image in order to complete the truncated part of said first image.

2. Method according to claim 1, wherein the second image is truncated, and wherein an item of information from the first image is introduced in the second image in order to complete the truncated part of the second image.

3. Method according to claim 1, wherein an angle α between a normal to the detection surface at said first angular position and a normal to the detection surface at said second angular position is less than approximately 10°.

4. Method according to claim 1, wherein the first image comprises an image of an edge of the patient's body, and wherein the second image comprises an image of an opposite edge of the patient's body.

5. Method according to claim 1, wherein a continuity is imposed between the information introduced in the truncated part of a projection and information acquired in said projection.

6. Method according to claim 1, further comprising obtaining a reconstructed tomographic image by acquiring images in projection of the patient's body taken from different angles α(i).

7. Method according to claim 1, wherein the images are acquired in emission.

8. Method according to claim 1, wherein the images are acquired in transmission.

9. Method according to claim 1, wherein the first and second images are acquired in tomography.

10. Method according claim 9, wherein, the tomography is a cardiac tomography with attenuation correction.

11. Method according to claim 9, wherein, prior to the tomographic examination, the detector head is placed in a position making it possible to determine the dimensions of the patient's body and its center C.

12. Method according to claim 11, wherein the first and second images are acquired without truncating a heart of the patient.

13. Method according to claim 9, wherein p of n images in projection are acquired according to a first trajectory of the detecting surface, and n-p other images are acquired according to a second trajectory of said detector surface.

14. Method according to claim 13, wherein the first trajectory comprises an inner edge of the field of detection of the detector head and follows the edges of the patient's body.

15. Method according to claim 13, wherein the second trajectory comprises an edge of the field of detection opposite the inner edge and follows the edges of the patient's body.

16. A method of obtaining an image of a patient's body, comprising the steps of:

placing the patient's body on a bed of a machine;

acquiring a first image in nuclear projection of the patient's body, said first image being acquired at a first angular position with respect to the patient's body and having a truncated part so as not to encompass an entire cross-section of the patient's body, acquiring a second image in nuclear projection of the patient's body, said second image being acquired at a second angular position with respect to the patient's body and encompassing a portion of the cross-section of the patient's body that is truncated from the first image, and introducing an item of information from said second image into said first image so as to complete the truncated part of said first image.

17. A method as defined in claim 16, wherein the second image has a truncated part so as not to encompass the entire cross-section of the patient's body.

18. A method as defined in claim 17, wherein the truncated part of the second image does not overlap the truncated part of the first image.

19. A method as defined in claim 18, wherein the truncated part of the first image includes a first edge of the patient's body and the truncated part of the second image includes a second edge of the patient's body disposed opposite said first edge.

20. A method as defined in claim 16, wherein said first and second images are acquired by the same detector head.

21. A method of obtaining an image of a patient's body, comprising the steps of:

placing the patient's body on a bed of a machine, said machine including a detector head equipped with a detection surface for detecting nuclear rays;

setting said detector head at a location in which the detector surface is disposed at first angular position with respect to the patient's body;

while said detector surface of said detector head is in said first angular position, acquiring a first image in projection of the patient's body, said first image having a truncated part so as not to encompass an entire cross-section of the patient's body, moving said detector head to a location in which the detector surface is disposed at a second angular position with respect to the patient's body, while said detector surface of said detector head is in said second angular position, acquiring a second image in projection of the patient's body, said second image encompassing a portion of the cross-section of the patient's body that is truncated from the first image, and introducing an item of information from said second image into said first image so as to complete the truncated part of said first image.

* * * * *